(12) United States Patent
Burroughs et al.

(10) Patent No.: US 7,195,623 B2
(45) Date of Patent: Mar. 27, 2007

(54) KIT INCLUDING SIDE FIRING SYRINGE NEEDLE FOR PREPARING A DRUG IN AN INJECTION PEN CARTRIDGE

(75) Inventors: Andrew Christopher Burroughs, Kenosha, WI (US); Shu Kun Chang, Evanston, IL (US); Mark James Fisher, Highland Park, IL (US); Benjamin L Rush, Evanston, IL (US); Richard Charles Thorne, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 300 days.

(21) Appl. No.: 10/473,285

(22) PCT Filed: Mar. 21, 2002

(86) PCT No.: PCT/US02/06646

§ 371 (c)(1),
(2), (4) Date: Dec. 19, 2003

(87) PCT Pub. No.: WO02/076374

PCT Pub. Date: Oct. 3, 2002

(65) Prior Publication Data

US 2004/0116892 A1    Jun. 17, 2004

Related U.S. Application Data

(60) Provisional application No. 60/279,074, filed on Mar. 27, 2001.

(51) Int. Cl.
*A61M 5/32* (2006.01)
*A61B 19/00* (2006.01)
(52) U.S. Cl. .................. 604/411; 604/415; 604/232; 604/187
(58) Field of Classification Search ............... 604/403, 604/411, 415, 416, 187, 86–88, 200, 201, 604/203, 218, 232, 181
See application file for complete search history.

(56) References Cited

U.S. PATENT DOCUMENTS 1,967,439 A    7/1934    Heineman
(Continued)

FOREIGN PATENT DOCUMENTS

WO    WO 93/05835    4/1993
(Continued)

OTHER PUBLICATIONS http://www.victor-g.com, disclosure regarding cannula, Oct. 2000.
(Continued)

*Primary Examiner*—Patricia Bianco
*Assistant Examiner*—Leslie R. Deak
(74) *Attorney, Agent, or Firm*—Edward J. Prein

(57) ABSTRACT

A kit and needle assembly for reconstituting a quantity of a lyophilized pharmaceutical. The kit of the invention may include a reconstituting appliance having a non-transparent needle covering portion with a hollow adapted to receive the inserted stoppered end of the injection pen cartridge, which needle covering portion extends around a side-firing cannula to hide the cannula from side view. A shiftable alignment member retained within the needle covering portion at a first axial position, and shiftable to a second axial position when abutted by the injection pen cartridge during its insertion, may be included. The kit includes an injection pen cartridge including a barrel filled with a quantity of a lyophilized drug, a slidable plunger used during pen operation to eject the reconstituted drug, and a stopper penetrable by the cannula during drug reconstituting. The needle assembly of the invention may include a cannula defining an axial passage therethrough in communication with a reservoir of diluent fluid. The distal end of the cannula terminates in a closed piercing tip, and is provided with a side port, in communication with the axial passage, which is configured to direct fluid passing through it in a direction diverging from the axis of the cannula. A collar fixedly mounted around a portion of the cannula defines an axial venting passageway therebetween, and the collar has a piercing distal end. A method for reconstituting a quantity of a lyophilized drug in an injection pen cartridge is also disclosed.

9 Claims, 11 Drawing Sheets

U.S. PATENT DOCUMENTS

| | | | |
|---|---|---|---|
| 2,541,272 A | 2/1951 | Murphy | |
| 2,973,758 A | 3/1961 | Murrish | |
| 3,063,451 A | 11/1962 | Kowalk | |
| 3,080,866 A | 3/1963 | Friedman | |
| 3,563,373 A | 2/1971 | Paulson | |
| 3,602,272 A | 8/1971 | Stawski | |
| 3,608,550 A | 9/1971 | Stawski | |
| 3,941,171 A | 3/1976 | Ogle | |
| 4,058,121 A | 11/1977 | Choksi et al. | |
| 4,296,786 A | 10/1981 | Brignola | |
| 4,537,593 A | 8/1985 | Alchas | |
| 4,564,054 A | 1/1986 | Gustavsson | |
| 4,610,683 A | 9/1986 | Vaillancourt | |
| 4,673,404 A | 6/1987 | Gustavsson | |
| 4,723,955 A | 2/1988 | Vaillancourt | |
| 4,787,898 A | 11/1988 | Raines | |
| 5,171,214 A | 12/1992 | Kolber et al. | |
| 5,226,900 A | 7/1993 | Bancsi et al. | |
| 5,240,047 A | 8/1993 | Hedges | |
| 5,247,972 A | 9/1993 | Tetreault | |
| 5,281,198 A * | 1/1994 | Haber et al. | 604/86 |
| 5,292,318 A | 3/1994 | Haber et al. | |
| 5,334,162 A | 8/1994 | Harris | |
| 5,454,409 A | 10/1995 | McAffer et al. | |
| 5,454,786 A * | 10/1995 | Harris | 604/88 |
| 5,466,220 A | 11/1995 | Brenneman | |
| 5,520,659 A | 5/1996 | Hedges | |
| 5,634,906 A | 6/1997 | Haber et al. | |
| 5,709,668 A | 1/1998 | Wacks | |
| 5,752,940 A * | 5/1998 | Grimard | 604/181 |
| 5,827,262 A | 10/1998 | Neftel et al. | |
| 5,843,043 A | 12/1998 | Markus | |
| 5,860,456 A | 1/1999 | Bydlon et al. | |
| 5,873,856 A | 2/1999 | Hjertman et al. | |
| 5,873,872 A | 2/1999 | Thibault et al. | |
| 5,893,397 A | 4/1999 | Peterson et al. | |
| 5,925,029 A | 7/1999 | Jansen et al. | |
| 5,957,166 A * | 9/1999 | Safabash | 141/26 |
| 5,980,491 A | 11/1999 | Hansen | |
| 6,070,623 A | 6/2000 | Aneas | |
| 6,071,270 A | 6/2000 | Fowles et al. | |
| 6,113,583 A | 9/2000 | Fowles et al. | |
| 6,149,623 A | 11/2000 | Reynolds | |
| 6,159,192 A | 12/2000 | Fowles et al. | |
| 6,183,446 B1 | 2/2001 | Jeanbourquin | |
| 6,280,430 B1 | 8/2001 | Neftel et al. | |
| 6,358,236 B1 | 3/2002 | DeFoggi et al. | |
| 2001/0051793 A1 | 12/2001 | Weston | |
| 2002/0173752 A1 | 11/2002 | Polzin | |
| 2002/0189705 A1 | 12/2002 | Reihl et al. | |

FOREIGN PATENT DOCUMENTS

| | | |
|---|---|---|
| WO | WO 97/20536 | 6/1997 |
| WO | WO 99/08036 | 2/1999 |
| WO | WO 00/54723 | 9/2000 |
| WO | WO 01/17478 | 3/2001 |
| WO | WO 01/60311 | 8/2001 |

OTHER PUBLICATIONS http://catalog.bd.com, disclosure regarding pharmacy products, Oct. 2000.

http://products.baxa.com, disclosure regarding product list, Oct. 2000.

*One Design Matters*, Apr./May 2001; "White Reset", p. 99.

* cited by examiner

KIT INCLUDING SIDE FIRING SYRINGE NEEDLE FOR PREPARING A DRUG IN AN INJECTION PEN CARTRIDGE

This application is related to and claims priority under 35 USC § 119 to U.S. Application Ser. No. 60/279,074, filed Mar. 27, 2001, the entire contents of which are incorporated by reference herein.

BACKGROUND OF THE INVENTION

The present invention pertains to reconstituting lyophilized drugs for use, and more particularly to a needle assembly, kit, and method for preparing a quantity of a lyophilized drug in an injection pen cartridge for use.

Due to a short shelf life or other difficulties in storage or transport, many drugs, such as human growth hormone, are lyophilized or freeze-dried for storage and transported in a powdered state. These drugs must then be reconstituted with water or another diluent fluid before use. Typically, a quantity of the powdered drug is stored in a vial sealed with a needle penetrable stopper. When the drug is needed, the stopper is penetrated with a syringe needle and the reconstituting fluid is added to the vial for mixing with the powdered drug. Once the drug is prepared, the mixed fluid is withdrawn from the container and administered in desired doses.

However, with many such drugs the fluid stream should not be injected directly onto the powdered drug as direct application can cause foaming, spraying and/or incorrect mixing. Further, if the fluid is added without a corresponding release of gas pressure from the vial, the pressure inside the vial can increase, potentially interfering with the reconstituting effect, interfering with fluid flow or potentially damaging the vial or syringe. This can cause difficulty in removing the drug for administration. Additionally, sufficient pressure in the vial can result in the drug or liquid being blown past the needle in the stopper. This condition, known as "blowback," can create inaccuracies in drug concentration and effective dosage.

One needle assembly for transferring liquid to or from a vial is suggested in U.S. Pat. No. 4,537,593 to Alchas. Alchas suggests a needle assembly beginning with a hub attachable to a syringe and terminating in a needle with a closed distal end having a protruding knife-blade with a width greater than the needle. A slot which serves as a side port is provided near the end of the needle through which liquid is introduced or withdrawn. In one form, a slidable sleeve is located between the needle hub and the protruding knife-blade. In use, Alchas suggests that the knife-blade should be pushed through the vial stopper, whereupon the stopper pushes the slidable sleeve upwards on the needle until it abuts the needle hub, and by continuing introduction of the needle, the sleeve then penetrates the stopper. In another form, the sleeve is fixed to the needle. After needle introduction, the liquid is then injected through the side slot into the vial, with air venting between the sleeve and needle during such liquid injection.

While functional, the Alchas design is not without its shortcomings. For one thing, the needle assembly, which is readily visible in use, may have a menacing appearance to some users. Moreover, as the needle assembly is suggested by Alchas to be used multiple times to transfer material to multiple containers, this use raises concerns of contamination of the drug or needle assembly during use. Still further, the knife-blade of the needle assembly may cause mechanical damage to a stopper which may compromise its ability to form an adequate seal.

One prior kit for reconstituting a drug in an injection pen cartridge is illustrated in FIGS. 1 and 2. In this kit, the needle of the syringe is inserted into a cartridge through an adapter, which forces the needle to be held at an angle to the cartridge wall, directing the diluent fluid at a wall of the cartridge. However, so injecting the diluent fluid may be more difficult or time-consuming than desired due to the need to displace gas in the cartridge with diluent. In particular, unless a user wiggles the syringe during the injection process to allow gas to escape from the cartridge through temporary passages between the needle and stopper, a user normally needs to press the syringe plunger rod to inject some diluent, allow gas to percolate from the cartridge through the injection needle and up to the syringe plunger, and then press or pump the plunger rod again, and repeat the process as needed, until the diluent is emptied from the syringe.

Consequently, it would be desirable to provide an apparatus and a method that overcomes these and other shortcomings of the prior art.

BRIEF SUMMARY OF THE INVENTION

According to one embodiment of the present invention, a needle assembly is provided for reconstituting a quantity of a lyophilized pharmaceutical in an injection pen cartridge. The needle assembly includes a cannula with a proximal end, a distal end and an external diameter, wherein the cannula is adapted to be mounted at its proximal end to a syringe with a fluid reservoir. The cannula defines an axial passage therethrough in communication with the fluid reservoir, and has a distal end terminating in a closed piercing tip. The distal end of the cannula defines a side port in communication with the axial passage. The side port is configured to direct fluid passing through it in a direction diverging from the cannula axis. A collar is fixedly mounted around a portion of the cannula and defines a passageway between the collar and the cannula. The collar has a piercing distal end.

An alternate embodiment is a kit for reconstituting a quantity of a lyophilized drug in a cartridge to be used in an injection pen. The kit includes an injection pen cartridge, which has a barrel with at least one interior wall defining an internal reservoir, which is partially filled with a quantity of a lyophilized drug. The barrel has an open proximal end and an open distal end. A needle penetrable stopper seals the proximal end of the barrel and has a stopper height. A plunger is slidably disposed within the distal end of the barrel in sealed engagement with the interior of the reservoir. The kit further includes a needle assembly associated with a fluid reservoir, which contains a diluent fluid. The needle assembly is operable to selectively inject the diluent fluid into the internal reservoir of the cartridge. The needle assembly includes a cannula with a proximal end in communication with the fluid reservoir, a closed distal end and an external diameter. The cannula defines an axial passage therethrough in communication with the fluid reservoir, wherein the cannula has a length greater than the stopper height and wherein the distal end of the cannula terminates in a piercing tip. The distal end of the cannula defines a side port in communication with the axial passage. The side port is configured to direct fluid passing through it towards the interior wall of the barrel of the cartridge at an angle diverging from the axial direction of the cannula A cylindrical collar is fixedly mounted around a portion of the cannula and defines an axial passage between the cannula and the collar. The collar has a length greater than the stopper height and the distal end of the collar terminates in a piercing edge.

In a further embodiment, the invention includes a kit for reconstituting a quantity of a lyophilized drug in a cartridge to be used in an injection pen. The kit includes an injection pen cartridge and a reconstituting appliance. The injection pen cartridge has a barrel with at least one interior wall defining an internal reservoir partially filled with a quantity of a lyophilized drug and having an open proximal end and an open distal end, a needle-penetrable stopper in sealed engagement with the proximal end of the barrel, and a plunger slidably disposed within the distal end of the barrel and in sealed engagement with the interior wall of the barrel. The reconstituting appliance has a syringe body with at least one interior wall defining a fluid reservoir containing a diluent fluid and having an open proximal end and an open distal end, a plunger slidably disposed within the proximal end of the syringe body and in sealed engagement with the interior wall of the syringe body, an actuating member extending from the plunger beyond the proximal end of the syringe body and manually shiftable to effect movement of the plunger to force diluent fluid from the fluid reservoir through the open distal end of the syringe body, and a cannula defining an axial passage therethrough and having a proximal end and a closed distal end. The cannula proximal end is in communication with the fluid reservoir through the open distal end of the syringe body, and the cannula has a length greater than a height of the stopper height. The distal end of the cannula terminates in a piercing tip and defines a side port in communication with the axial passage, which side port is configured to direct fluid passing therethrough toward the interior wall of the barrel of the cartridge at an angle diverging from the axial direction of the cannula. The reconstituting appliance also includes a housing having a non-transparent needle covering portion extending around the cannula, which needle covering portion includes a distal end and a proximal end. The needle covering portion distal end has an opening in communication with an interior hollow of the needle covering portion which is structured and arranged to receive the proximal end of the barrel of the injection pen cartridge when inserted proximally within the opening. The distal end of the needle covering portion is positioned distally of the cannula distal end, and the proximal end of the needle covering portion is positioned proximally of the cannula proximal end, whereby the cannula is hidden from side view by the needle covering portion as the cannula is introduced through the stopper of the injection pen cartridge.

In a still further embodiment, the invention includes a kit for reconstituting a quantity of a lyophilized drug in a cartridge to be used in an injection pen. The kit includes an injection pen cartridge and a reconstituting appliance. The injection pen cartridge has a barrel with at least one interior wall defining an internal reservoir partially filled with a quantity of a lyophilized drug and having an open proximal end and an open distal end, a needle-penetrable stopper in sealed engagement with the proximal end of the barrel, and a plunger slidably disposed within the distal end of the barrel and in sealed engagement with the interior wall of the barrel. The reconstituting appliance has a syringe body with at least one interior wall defining a fluid reservoir containing a diluent fluid and having an open proximal end and an open distal end, a plunger slidably disposed within the proximal end of the syringe body and in sealed engagement with the interior wall of the syringe body, an actuating member extending from the plunger beyond the proximal end of the syringe body and manually shiftable to effect movement of the plunger to force diluent fluid from the fluid reservoir through the open distal end of the syringe body, and a cannula defining an axial passage therethrough and having a proximal end and a closed distal end. The cannula proximal end is in communication with the fluid reservoir through the open distal end of the syringe body. The cannula has a length greater than a height of the stopper. The distal end of the cannula terminates in a piercing tip and defines a side port in communication with the axial passage, which side port is configured to direct fluid passing therethrough toward the interior wall of the barrel of the cartridge at an angle diverging from the axial direction of the cannula. The reconstituting appliance also has a housing having a needle covering portion extending around the cannula, which needle covering portion includes a distal end having an opening in communication with an interior hollow of the needle covering portion which is structured and arranged to receive the proximal end of the barrel of the injection pen cartridge when inserted proximally within the opening, wherein the distal end of the needle covering portion is positioned distally of the cannula distal end. The reconstituting appliance also has a cartridge alignment member retained within the needle covering portion at a first axial position and defining an interior hollow structured and arranged to receive the proximal end of the barrel of the injection pen cartridge when the cartridge is proximally inserted through the opening of the needle covering portion distal end. The cartridge alignment member is adapted to be abutted by the injection pen cartridge during proximal insertion of the cartridge and axially shifted relative to the needle covering portion to a second axial position at which the cannula extends through the stopper of the injection pen cartridge for drug reconstituting. The cannula distal end is hidden from side view by at least one of the needle covering portion and the cartridge alignment member as the cannula is introduced through the stopper of the injection pen cartridge.

In a still further embodiment, the present invention includes a method for reconstituting a quantity of a lyophilized drug in an injection pen cartridge, including the steps of: providing an injection pen cartridge including a cartridge reservoir partially filled with a quantity of a lyophilized drug, wherein the cartridge is sealed with a needle penetrable stopper at one end and sealed with a plunger at the opposing end; providing a reconstituting appliance which holds a quantity of diluent fluid and includes a needle and a housing, wherein the housing hides the needle from lateral view and defines an interior hollow around the needle which is shaped to accommodate the cartridge end with the stopper; inserting the cartridge end with the stopper into the housing interior hollow such that the needle penetrates the stopper, wherein the needle terminates in a distal end within the cartridge reservoir; laterally injecting the quantity of diluent fluid through a side port in the distal end of the needle into the cartridge reservoir above the level of the lyophilized drug; and, after fluid injection, withdrawing the cartridge end with the stopper from the housing interior hollow, whereby the needle is removed from the stopper.

One advantage of the present invention is that an improved kit, needle assembly and method for reconstituting a lyophilized drug in an injection pen cartridge can be provided.

Another advantage of the present invention is that a reconstituting appliance can be provided with a hidden needle so as to make the use of the appliance less upsetting to some users.

Still another advantage of the present invention is that a reconstituting appliance can be provided which signals an attentive user when an injection pen cartridge has been properly mounted to the appliance for reconstituting of the lyophilized drug contained in that cartridge.

Still another advantage of the present invention is that a needle assembly can be provided which allows the drug reconstituting process to be performed more quickly than previously possible with some known devices, and with limited mechanical damage to a rubber stopper intended to seal the drug product.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taking in conjunction with the accompanying drawings, wherein.

Figure 1:
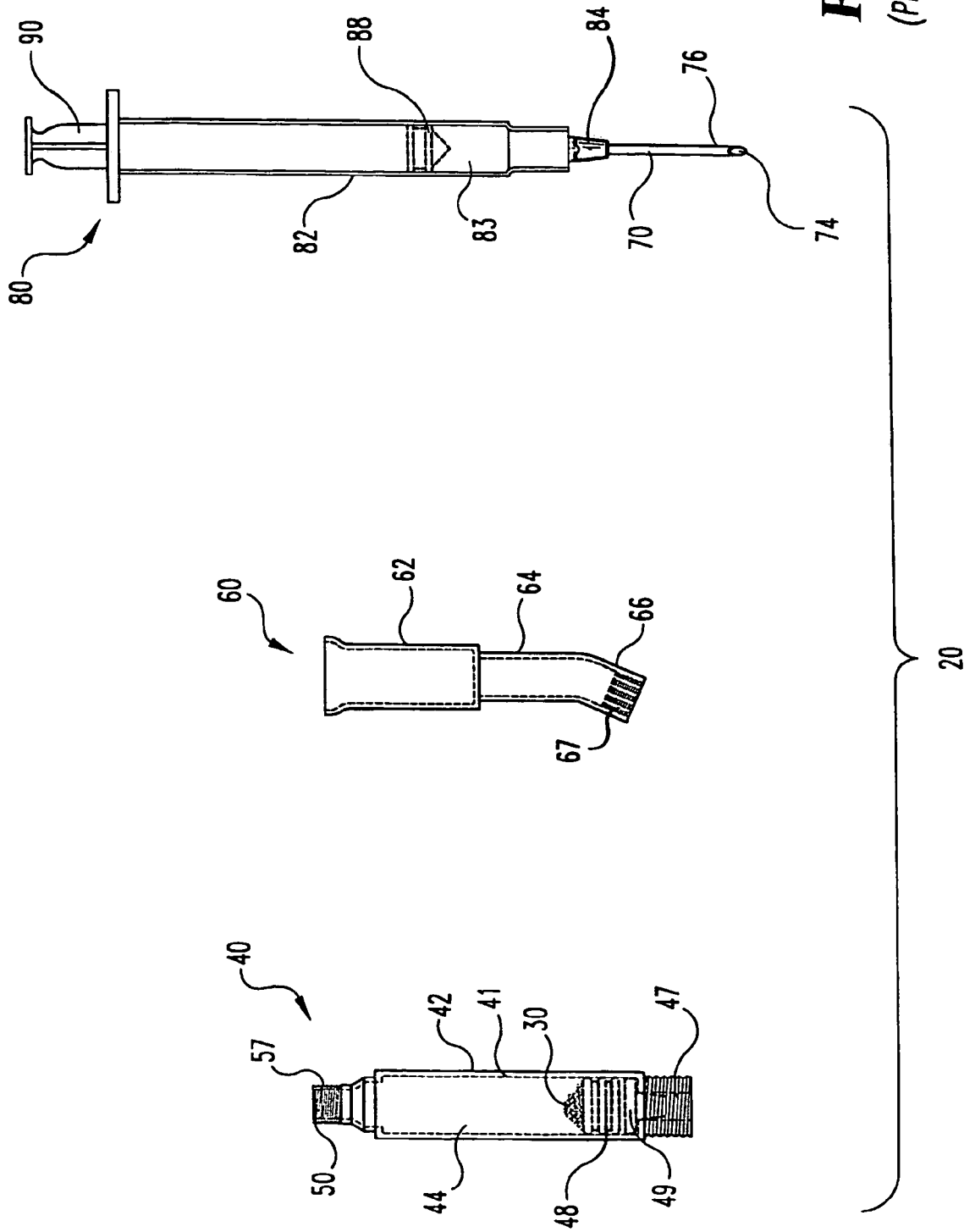
FIG. 1 is an illustration of the separate components of a prior art kit.

Corresponding reference characters indicate corresponding parts throughout the several views. Although the drawings represent multiple embodiments of the present invention, the drawings are not necessarily to scale, and certain features may be exaggerated or omitted in some of the drawings in order to better illustrate and explain the present invention.

DETAILED DESCRIPTION OF THE INVENTION

For the purposes of promoting an understanding of the principles of the invention, reference will now be made to the embodiments illustrated herein, and specific language will be used to describe the same. It will nevertheless be understood that no limitation of the scope of the invention is thereby intended, such alterations, modifications, and further applications of the principles of the invention being contemplated as would normally occur to one skilled in the art to which the invention relates.

The present invention provides an improved kit, needle assembly and method for reconstituting a pharmaceutical compound in an injection pen cartridge. For ease of storage and stability, drugs, for example human growth hormone, are often lyophilized or freeze-dried. Thus, prior to use, the drug needs to be reconstituted with a diluent fluid, such as water. Frequently, such drugs have been stored in small containers closed with needle penetrable stoppers. The diluent fluid is injected into the container and mixed with the drug, after which the reconstituted drug is withdrawn into a syringe or similar equipment for injection. When the diluent fluid is injected, it is desirable to avoid directing the fluid stream directly onto the powdered drug to avoid foaming or spraying of the powder. Additionally, to avoid excess pressure in the container, there has been a need to vent excess gas pressure from the container as the diluent fluid is being injected.

Figure 2:
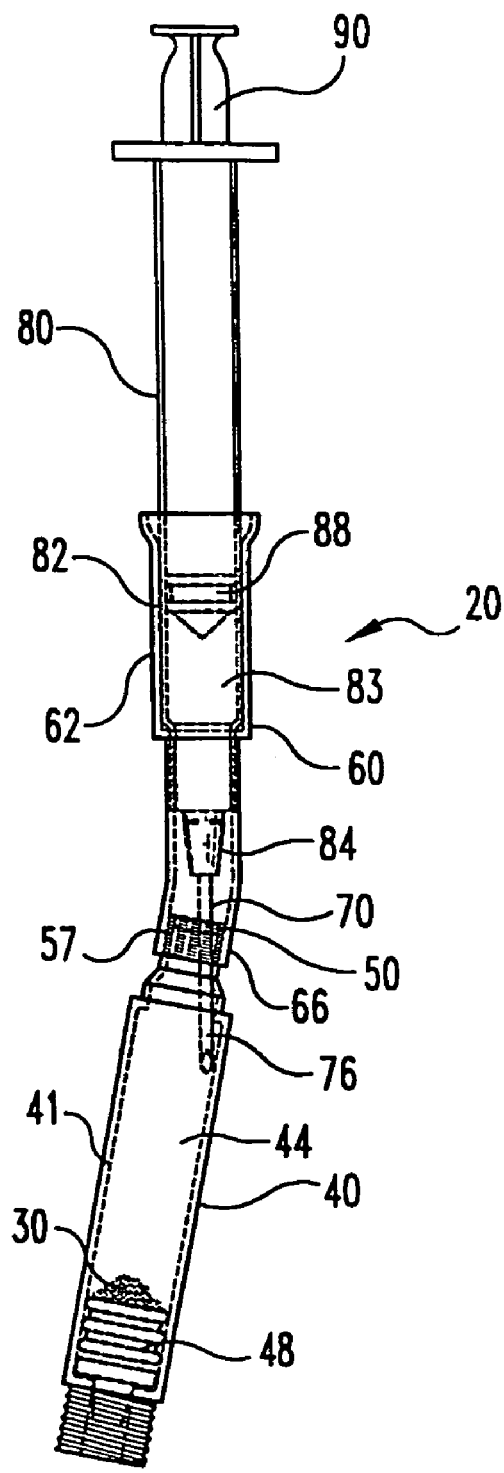
FIG. 2 is an illustration of the combined components of the prior art kit illustrated in FIG. 1.

Illustrated in FIGS. 1 and 2 is a prior art kit for reconstituting a drug 30 in an injection pen cartridge 40. Kit 20 includes injection pen cartridge 40, adapter 60, and syringe 80. Injection pen cartridge 40 is made with a barrel portion 42, which is preferably cylindrical and includes an interior wall 41 defining a reservoir 44. Although shown as having a single wall construction in FIG. 1 to facilitate illustration, cartridge 40 may include a double-wall construction, wherein a glass container is housed within an outer, protective plastic sleeve, and the interior wall of that glass container serves as interior wall 41. Reservoir 44 is closed at the proximal end 57 with a needle penetrable stopper 50, and is closed at the distal end 47 with plunger 48. Plunger 48 is slidably and sealably engaged with the interior wall 41 of barrel portion 42. Rod tip 49 distributes on plunger 48 a force applied by an injector pen drive member that advances within the cartridge in order to move the plunger. Distal end 47 is threaded for engagement with an injector pen as is known in the art, and proximal end 57 is threaded for engagement with adapter 60.

Adapter 60 includes receiver portion 62 connected to a distal portion 64 which is curved or bent before terminating in distal end 66. Distal end 66 is internally threaded to engage proximal end 57 of cartridge 40.

Syringe 80 includes a barrel portion 82 sized to be fitted within the interior channel of receiver portion 62 of adapter 60. Barrel portion 82 defines an internal reservoir 83 closed at the distal end with hub 84. The proximal end of reservoir 83 is closed with plunger 88 in slidable and sealed engagement with the interior wall of barrel portion 82. Plunger rod 90 may be used to slidably move plunger 88. Needle 70 has a proximal end mounted to hub 84 and terminates in distal end 76. This shown needle mounting using a hub 84 illustrates a luer lock construction, but the needle may instead be adhesively mounted to the distal end of the barrel portion. Interior axial channel 74 extends from distal tip 76 through needle 70 into hub 84 and communicates with reservoir 83.

When prior art kit 20 is used, as illustrated in FIG. 2, distal end 66 of adapter 60 is threaded into engagement with proximal end 57 of cartridge 40. Syringe 80 is placed in receiver portion 62 of adapter 60 as needle 70 is pushed through stopper 50 so that distal end 76 is positioned in the upper portion of reservoir 44 of cartridge 40. The angle in adapter 60 forces needle 70 to penetrate stopper 50 at an angle such that distal tip 76 of needle 70 is adjacent to and directed toward the internal wall of cartridge 40. This avoids the diluent fluid being directly aimed toward the drug 30.

An improved kit 120 is illustrated in FIGS. 3–6. Kit 120 includes injection pen cartridge 140 and a syringe with needle assembly, generally designated 180. Injection pen cartridge 140 is similar to cartridge 40 and includes barrel 142, internal wall 143 defining reservoir 144, stopper 150 at proximal end 157, and plunger 148 and rod tip 149 at distal end 147. Pen cartridge 140 does not require threads on proximal end 157, but threads can be provided if, for example, such are used to mount the stopper penetrating needle of the injector pen that penetrates the user's skin.

Syringe with needle assembly 180 includes barrel 182 including interior wall 181 defining internal reservoir 183 closed at the distal end by hub 184. Barrel 182 is closed at the proximal end by a slidable plunger 188 connected to rod 190. Barrel 182 and plunger 188 are preferably cylindrical, however other shapes known in the art can be used. Needle or cannula 170 is mounted at its proximal end to hub 184 and terminates in a distal end 176. Hub 184 may be an integral portion of the distal end of a syringe, or may be a part removably mounted, such as through a luer, to the syringe. Collar 160 is preferably fixedly mounted over a portion of cannula 170. In an alternate embodiment, the collar can be slidably mounted on the cannula, and prevented from sliding off the cannula by a slight deformation of the cannula that results from its preferred deflected tip construction.

Figure 4:
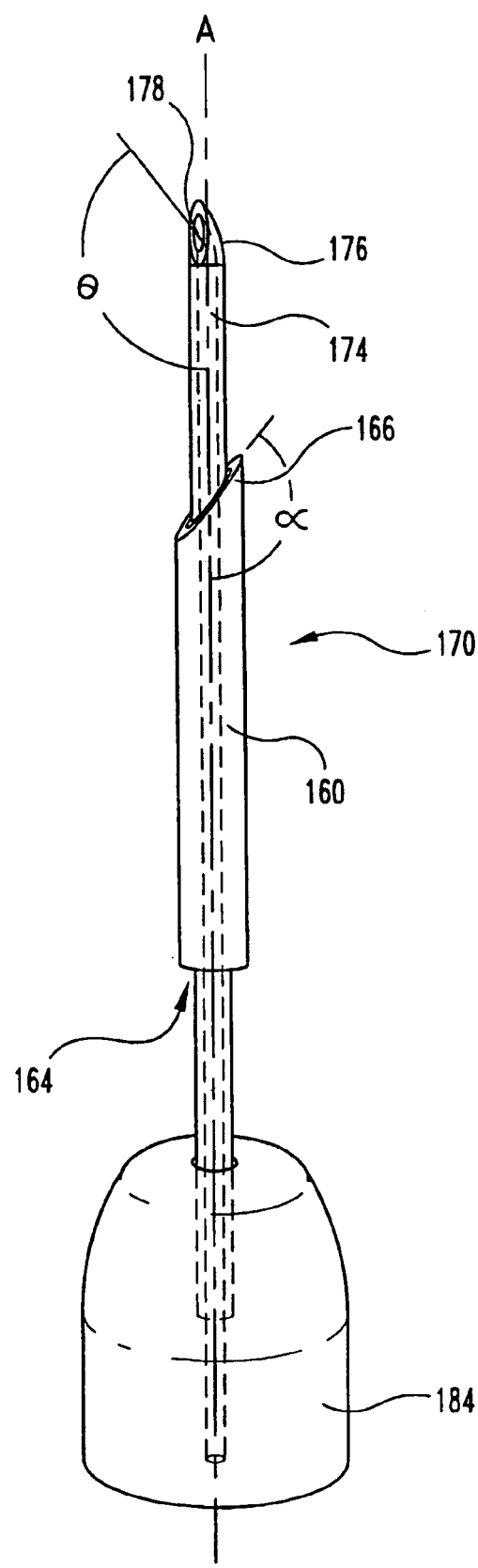
FIG. 4 is a detailed, enlarged view of one embodiment of a needle and collar used with the present invention.
Figure 5:
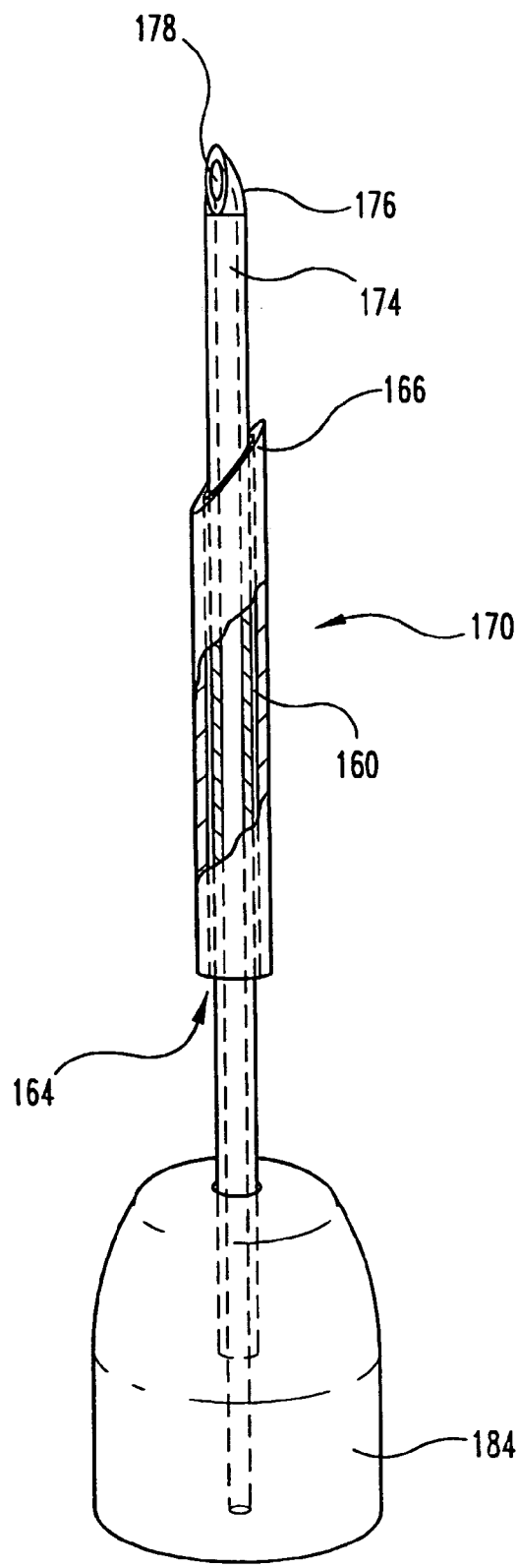
FIG. 5 is an enlarged, cut-away view of the embodiment of a needle and collar shown in FIG. 4.

As can be seen in enlarged views in FIGS. 4 and 5, cannula 170 includes axial interior channel 174 terminating adjacent the piercing tip of distal end 176 in side port 178. Side port 178 directs the diluent fluid laterally away from the axis A of cannula 170 at an angle $\theta$. Distal end 176 terminates in a closed sharpened point for piercing a stopper. The cannula with side port construction shown in FIGS. 4 and 5 is known as a deflected tip, but other side ports, including one or more axially or angularly spaced holes or slots which allow diluent to be fired to the side, may be provided in the distal end.

Similarly, distal end 166 of collar 160 terminates in a distal piercing edge for penetrating a stopper. Preferably the piercing edge of collar 160 is tapered at an angle $\alpha$ from cannula axis A. Preferably collar 160 has a circular cross-section and an interior diameter slightly greater than the exterior diameter of cannula 170 and a length greater than the height of stopper 150. The slight radial gap between collar 160 and needle 170 provides a passage 164 through which air or other gases can travel.

Figure 6:
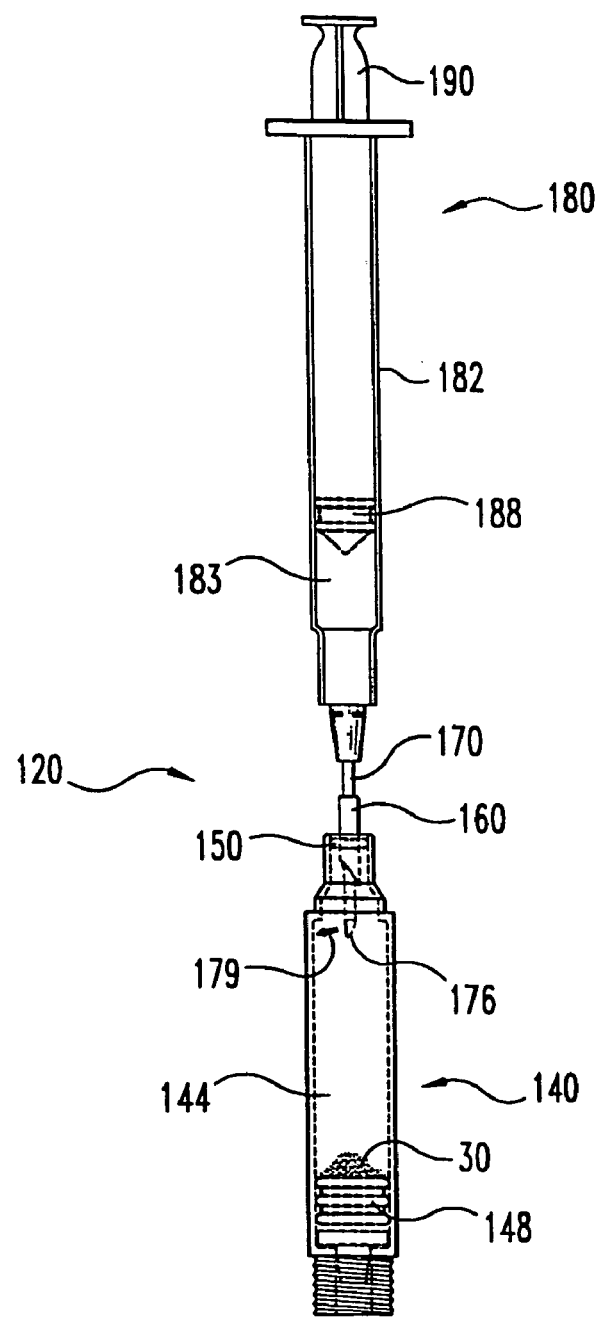
FIG. 6 is a side view of the combined components in one embodiment of the kit illustrated in FIG. 3.

A method of using kit 120 is illustrated in FIG. 6. When used, cannula 170 of syringe 180 is manually pressed perpendicularly into and through stopper 150 of cartridge 140. The user continues to push cannula 170 until collar 160 penetrates through the stopper as well. When inserted, collar 160 extends completely through stopper 150 providing a passageway communicating from the reservoir 144 to the outside of cartridge 140. Rod 190 is depressed, distally shifting plunger 188 to force fluid from syringe reservoir 183 through channel 174 and out through side port 178 as indicated at arrow 179. Side port 178 laterally directs the diluent fluid away from the axis A of the needle and toward the interior wall 143 of the cartridge 140. Distal end 176 of cannula 170 remains above the level of the lyophilized drug so that the diluent fluid is not directly applied to the drug. As the diluent fluid is introduced into reservoir 144, excess air pressure is bled off through passage 164 between cannula 170 and collar 160.

Once sufficient diluent fluid has been added to the cartridge, syringe 180 including cannula 170 and collar 160 are withdrawn, allowing stopper 150 to reseal. The simple perpendicular insertion and withdrawal of cannula 170 allows the diluent fluid to be delivered quickly without an adapter or threading pieces together.

Cartridge 140 may then be loaded and used in an injection pen. The threading of distal end 147 shown in FIG. 3 allows the cartridge to be loaded by screwing it onto a base of the injection pen. Other cartridge designs, which employ other manners of being loaded to injection pens, are within the scope of the invention.

In conventional fashion, the injection pen includes a plunger rod which enters the distal end of cartridge 140 and operationally engages cartridge plunger 148 via rod tip 149 to push the reconstituted-drug towards the proximal end of cartridge 140 and into an injection mechanism such as a needle mounted thereon. The injection pen can be adjusted to advance plunger 148 as necessary to deliver the desired pharmaceutical dose.

Cartridge 140 and syringe 180 are of standard medical-grade materials known in the art, such as glass, plastic and/or rubber. Cannula 170 and collar 160 are preferably manufactured from a medical-grade stainless steel with collar 160 preferably fixed in place on cannula 170 through crimping, laser or spot welding, adhesive, soldering or similar well known metal to metal contact techniques.

By way of illustration, cannula 170 could have a length of 0.875 inches terminating in a deflected tip type construction forming distal tip 176 with side port 178. It is preferred that the side port of the deflected tip be directed at an angle $\theta$ between about 90 and about 164 degrees from the cannula axis A. In one preferred configuration, the side port of the deflected tip is directed at an angle $\theta$ of about 155 degrees from the cannula axis. Similarly, for example, collar 160 can have a length of 0.370 inches ending in a distal piercing tip tapered at an angle $\alpha$ of 145 degrees from the cannula axis.

Figure 7:
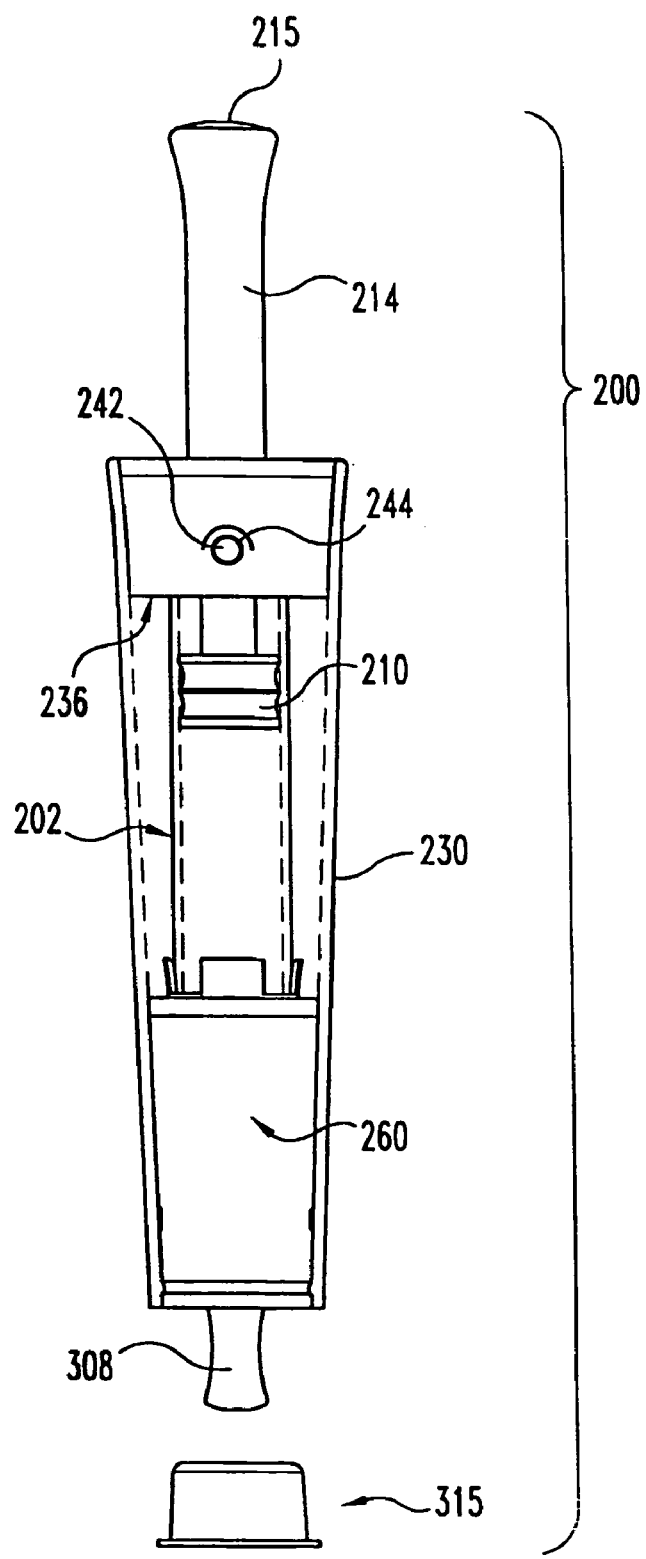
FIG. 7 is a side view of an alternate reconstituting appliance of a kit of the present invention.
Figure 8:
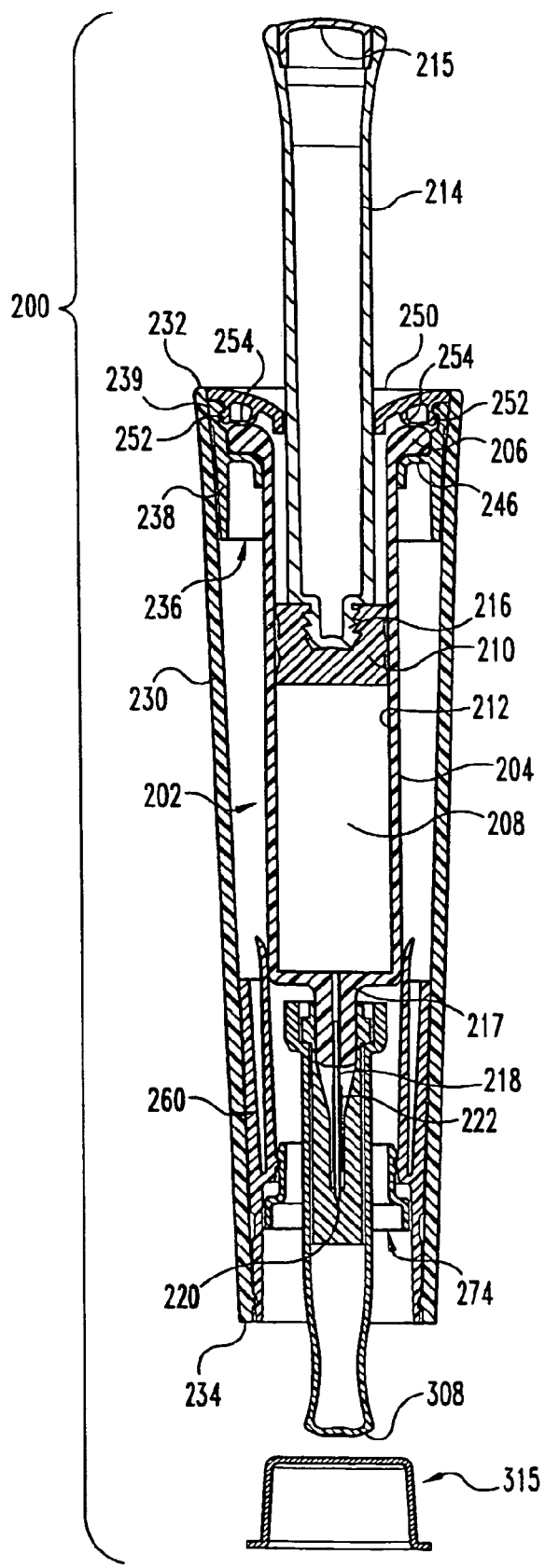
FIG. 8 is a cross-sectional side view of the reconstituting appliance illustrated in FIG. 7.

Referring now to FIGS. 7 and 8, there is respectively shown a side view and a cross-sectional side view of an alternate reconstituting appliance of the present invention. The reconstituting appliance, generally designated 200, may be substituted in kit 120 of FIG. 3 for syringe with needle assembly 180.

Figure 3:
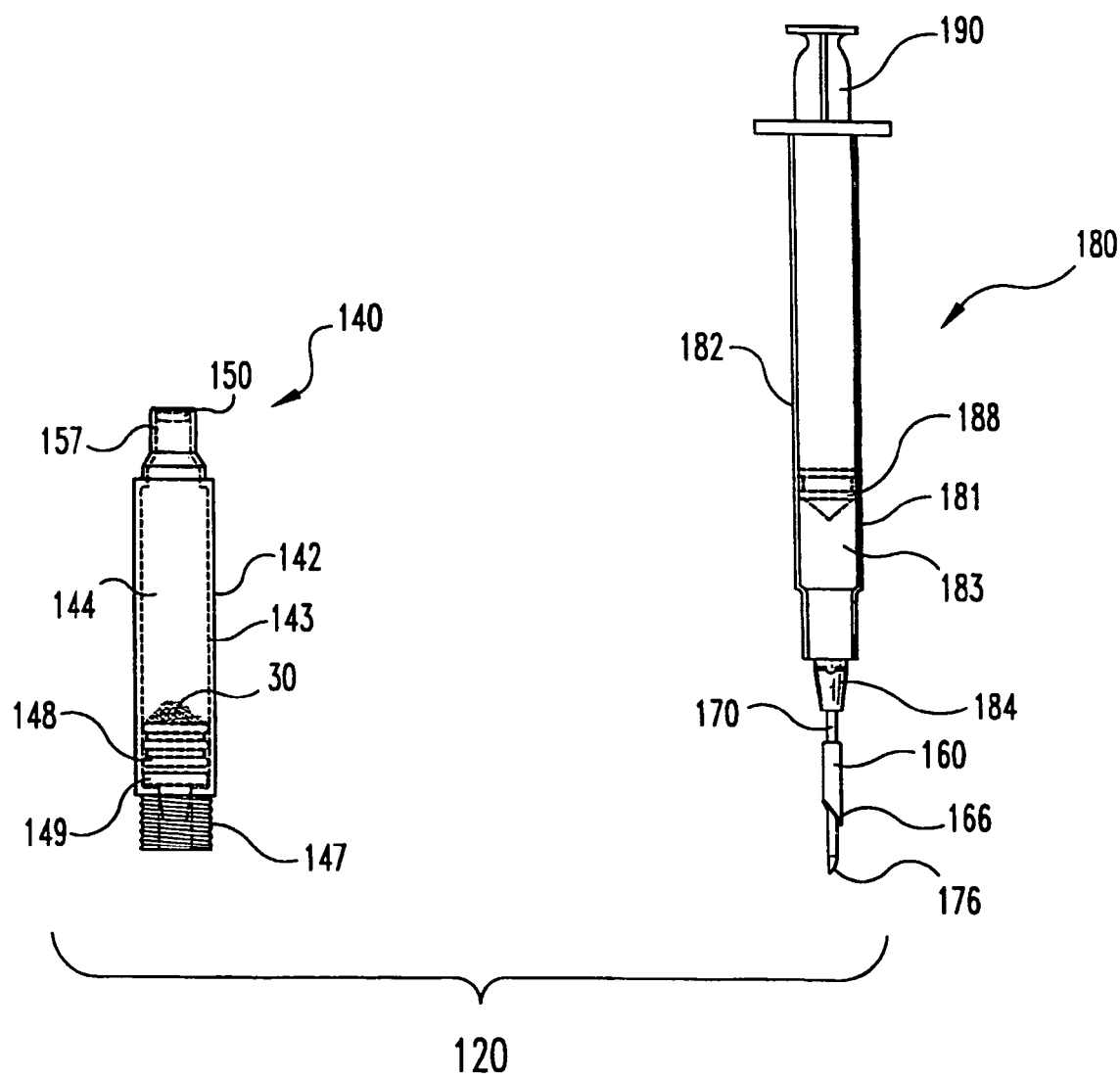
FIG. 3 is a side view of the separate components in one embodiment of a kit according to the present invention.

Reconstituting appliance 200 includes an external housing that holds a syringe and needle assembly which is related in design to that shown at 180 in the embodiment of FIG. 3. Specifically, a syringe 202 includes a barrel portion 204, which is preferably cylindrical and made of glass. Upper flange 206 radially extends from barrel portion 204 at the syringe proximal end, and is generally annular in shape except for a pair of not shown flats spaced 180 degrees apart on the outer radial periphery of the flange. Barrel portion 204 defines an internal fluid reservoir 208 closed at its proximal end with a plunger 210 in slidable and sealed engagement with the interior wall 212 of the barrel portion. Fluid reservoir 208 is filled with a diluent fluid required in the reconstitution process for which appliance 200 is intended for use.

A hollow plunger rod 214, made of a lightweight material such as plastic, is capped by plunger cap 215, made of a lightweight and resilient material such as plastic. Plunger rod 214 includes a threaded projection 216 at its distal end which screws into a threaded internal cavity of plunger 21. Plunger rod 214 projects above the appliance housing and may be manually depressed by a digit, typically the thumb, of the user to shift plunger 210 further into syringe 202 to dispense diluent fluid.

The distal end of fluid reservoir 208 is in flow communication with the proximal end of a needle 218 that is fixedly mounted to a hub portion 217 integrally formed as the distal end of barrel portion 204. In a preferred embodiment, needle 218 is side-ported or firing and terminates in closed distal end 220. Appliance 200 is shown equipped with a venting collar 222. In a not shown reconstituting appliance intended to reduce the likelihood that materials within an inserted cartridge can escape therefrom when that appliance, with the inserted cartridge, is inverted, no venting collar around needle 218 is provided. Needle 218 and collar 222 preferably are identical to the needle assembly shown in the embodiment of FIGS. 3–6, but other needle(s) achieving a diluent fluid introduction, preferably via side firing, may be employed within the scope of the invention.

The housing of reconstituting appliance 200 includes an outer tubular body 230 preferably formed of a transparent material, such as plastic, to allow visibility of the diluent fluid contained in syringe 202. Body 230 has a generally square with rounded corners shaped periphery at its upper end 232, which squarish periphery blends along the body height into a tapering cylindrical form that terminates at a distal end 234 having a circular periphery.

A shoulder 236 molded from plastic is inserted during assembly within the proximal internal region of body 230. Shoulder 236 includes a tubular base 238 shaped complementary to the body proximal internal region and which includes a circumferential stand-off 239 at its proximal end that abuts body 230 to create a small air space between the interior surface of body 230 and the rest of the exterior surface of shoulder base 238. A pair of resilient locking buttons 242 spaced 180 degrees apart along the circumference of shoulder base 238 project radially outward into holes 244 through body 230 to secure shoulder 236 thereto. An annular seating portion 246 of shoulder 236 supports the underside of syringe flange 206. Not shown posts of shoulder 236 which upwardly extend from seating portion 246 abut the peripheral flats of syringe flange 206 to prevent rotation of syringe 202 within body 230.

An annular shoulder cap 250, which is molded from plastic and through which plunger rod 214 extends, covers shoulder 236 within body 230. Cap 250 includes four depending, resilient latches 252, equally spaced around the cap circumference, that snap-fit within four corresponding recesses in the radial interior surface of shoulder base 238 to secure cap 250 to shoulder 236. A pair of not shown alignment tabs of cap 250 fit within radially aligned openings in shoulder 236 to help prevent cap 250 from rotating on shoulder 236. Two flexible fingers 254 arranged in an arcuate fashion on, and depending from, the cap underside are spaced 180 degrees apart and press syringe flange 206 against shoulder seating portion 246 to limit axial movement of syringe 202 within body 230.

Figure 9:
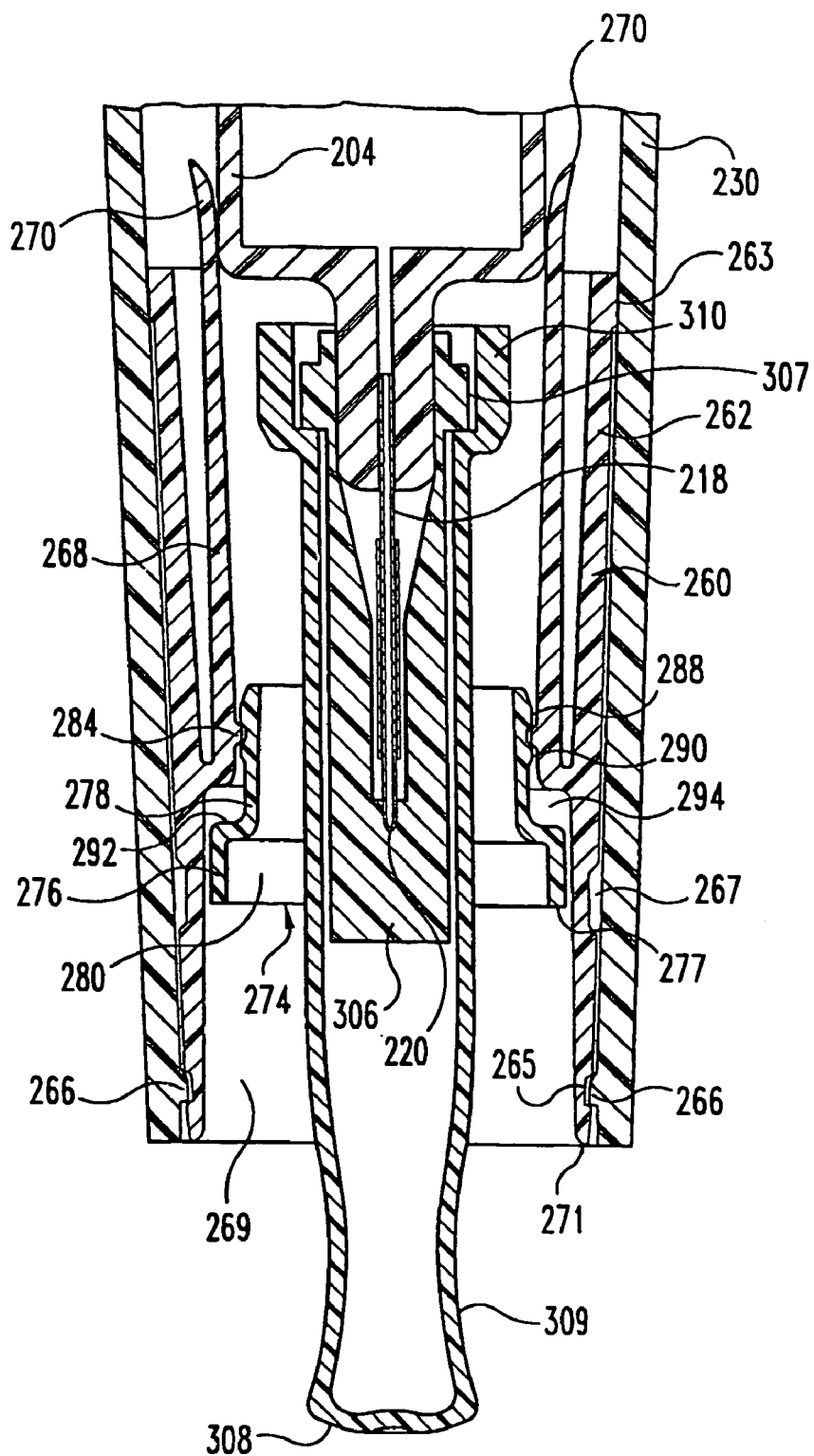
FIG. 9 is a cross-sectional, partial view of the reconstituting appliance illustrated in FIG. 7.

With additional reference to FIG. 9, a housing nose piece 260 molded from a lightweight material such as plastic is inserted during assembly within the distal internal region of body 230. As the central axial portion of nose piece 260 preferably serves as a needle cover to hide the needle from side view, nose piece 260 is opaque or otherwise non-transparent. A tubular base 262 of nose piece 260 is shaped complementary to the body distal internal region and includes a circumferential stand-off 263 at its proximal end that abuts the body 230 to create a small air space between the interior surface of body 230 and the rest of the exterior surface of nose piece base 262. A circumferential groove 265 on the outer radial periphery of nose piece base 262 in closely spaced relationship with its distal end accommodates four radially inwardly extending tabs 266 of body 230. Tabs 266, which are spaced at 90 degree intervals around the inner circumference of body 230, insert within groove 265 during manufacturing assembly to securely maintain nose piece 260 relative to body 230. A pair of notches 267 shown 180 degrees apart in the exterior of nose piece base 262 facilitate molding, but serve no purpose during appliance use.

Nose piece 260 further includes a cylindrical tubular portion 268 coaxially arranged with base 262 within its interior volume. The interior volume portion 269 of nose piece base 262 that is located distally of tubular portion 268 is sized to allow insertion therein of the proximal end of cartridge 140 of kit 120. Tubular portion 268 is integrally formed with and extends in a proximal direction from a central section of base 262. Four notches in the proximal end of tubular portion 268 define four angularly spaced flanges 270 that resiliently bend radially outward to hold in a friction fit the distal end of syringe barrel portion 204. Needle 218 axially extends within the interior volume of nose piece tubular portion 268, and interior volume portion 269. The closed distal end 220 of needle 218 is in fixed, spaced relationship with the distal end 271 of nose piece 260, and is therefore hidden when viewed from the side.

To aid a user in locating cartridge 140 within reconstituting appliance 200 to correctly engage needle 218 and collar 222, a shiftable, collar-shaped alignment member, generally designated 274, is preferably mounted within nose piece 260. Alignment collar 274 is adapted to be movable proximally within nose piece 260 during cartridge insertion so as to provide an indication to a user of correct cartridge installation.

Alignment collar 274 is made from a lightweight material such as plastic, and is opaque or otherwise non-transparent if nose piece 260 is made transparent and alignment collar 274 is intended to hide the needle from view. Alignment collar 274 includes a cylindrical base portion 276 with a stepped-down neck portion 278 that define an interior volume 280 shaped to receive proximal end 157 of cartridge 140. Collar neck portion 278 is designed complementary to nose piece tubular portion 268 to allow alignment collar 274 to be axially retained within nose piece 260 in a first or shipped position, and then to be axially movable relative to nose piece 260 to a use position for cartridge alignment purposes.

In a preferred embodiment, the complementary design includes a radially inward protruding section 284, such as a circumferential ridge, on nose piece tubular portion 268. Ridge 284 fits within a circumferential hollow defined by axially spaced, radially outward protruding sections 288 and 290 on the outer radial periphery of neck portion 278. As shown in FIG. 9, during this engagement the axial-facing collar shoulder 292 is in spaced relationship with the distal end of nose piece tubular portion 268 to define axial gap 294 therebetween.

Figure 11:
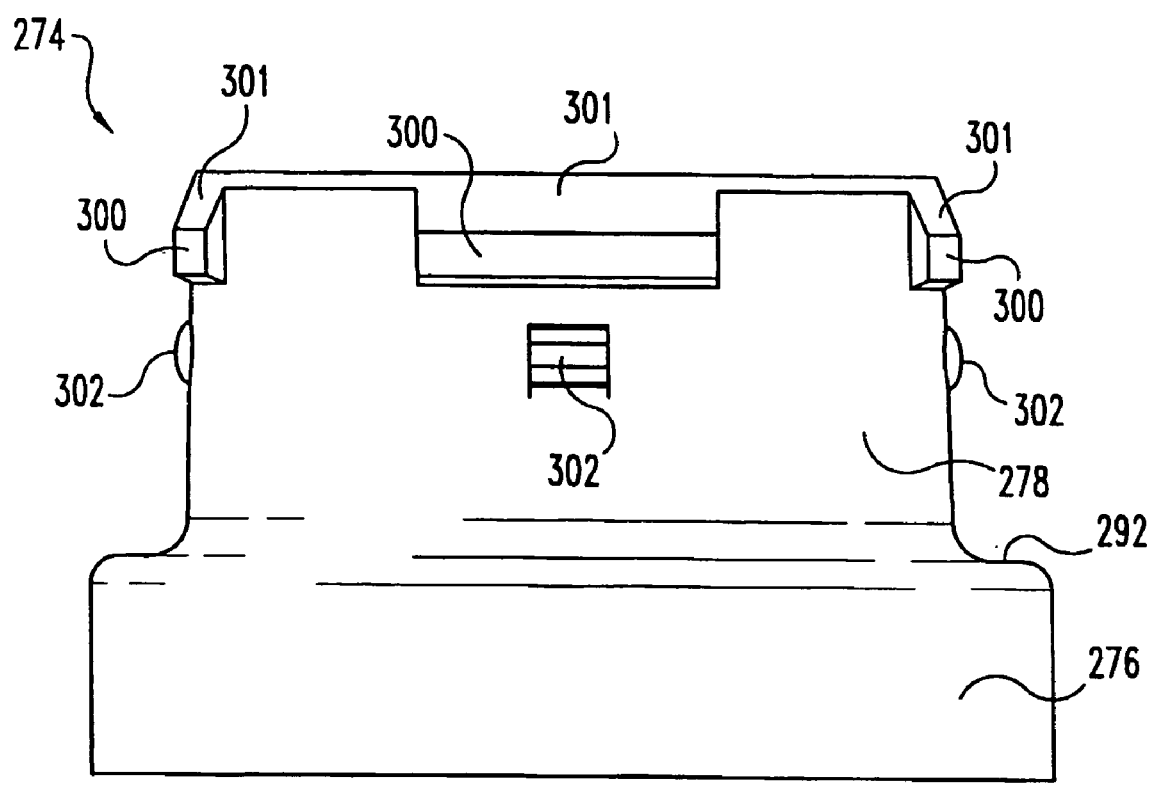
FIG. 11 is a side view of a preferred alignment collar shown separate from the reconstituting appliance of FIG. 7.

As further shown in FIG. 11, a preferred form of protruding section 288 is a circumferential ridge that is interrupted at four locations to define four equally angularly spaced ridge sections indicated at 300. Ramped proximal surfaces 301 facilitate slipping ridge sections 300 over nose piece ridge 284 during assembly by the manufacturer. Protruding section 290 is preferably formed by four detents 302 circumferentially spaced 90 degrees apart and each axially spaced from shoulder 292. Other complementary designs of nose piece 260 and alignment collar 274, such as by using uninterrupted protruding sections, or by altering the locations on the components of the connecting modules, may be utilized to shiftably retain the collar on the nose piece in alternate embodiments.

As best shown in FIG. 9, a removable needle shield assembly connectable to syringe hub 217 includes an elastomeric base 306 which friction fits to hub 217 and defines an internal hollow in which fits needle 218 and collar 222. Distal end 220 of needle 218 penetrates the base 306 at the inward end of the internal hollow a sufficient depth to seal the side port. A tip cover 308 of the needle shield assembly is molded from plastic and has an interior volume in which fits base 306. Cover 308 has a circumferential concavity 309 near its distal end which provides an ergonomic region to manually grip to pull off the needle shield assembly from the position shown in FIGS. 7–9 in order to use appliance 200. A pair of not shown flanges of cover 308 within expanded region 310 radially inwardly protrude above collar 307 of base 306 to hold cover 308 on base 306 such that the needle shield assembly remains together when the cover 308 is gripped and pulled for removal.

In FIGS. 7 and 8, an optional end cap is also shown. End cap 315 maybe used to plug the opening at distal end 234 of body 230 after the needle shield assembly has been removed and the appliance 200 used, such that the removed needle shield assembly need not be reinserted over needle 218 for disposal.

Figure 10:
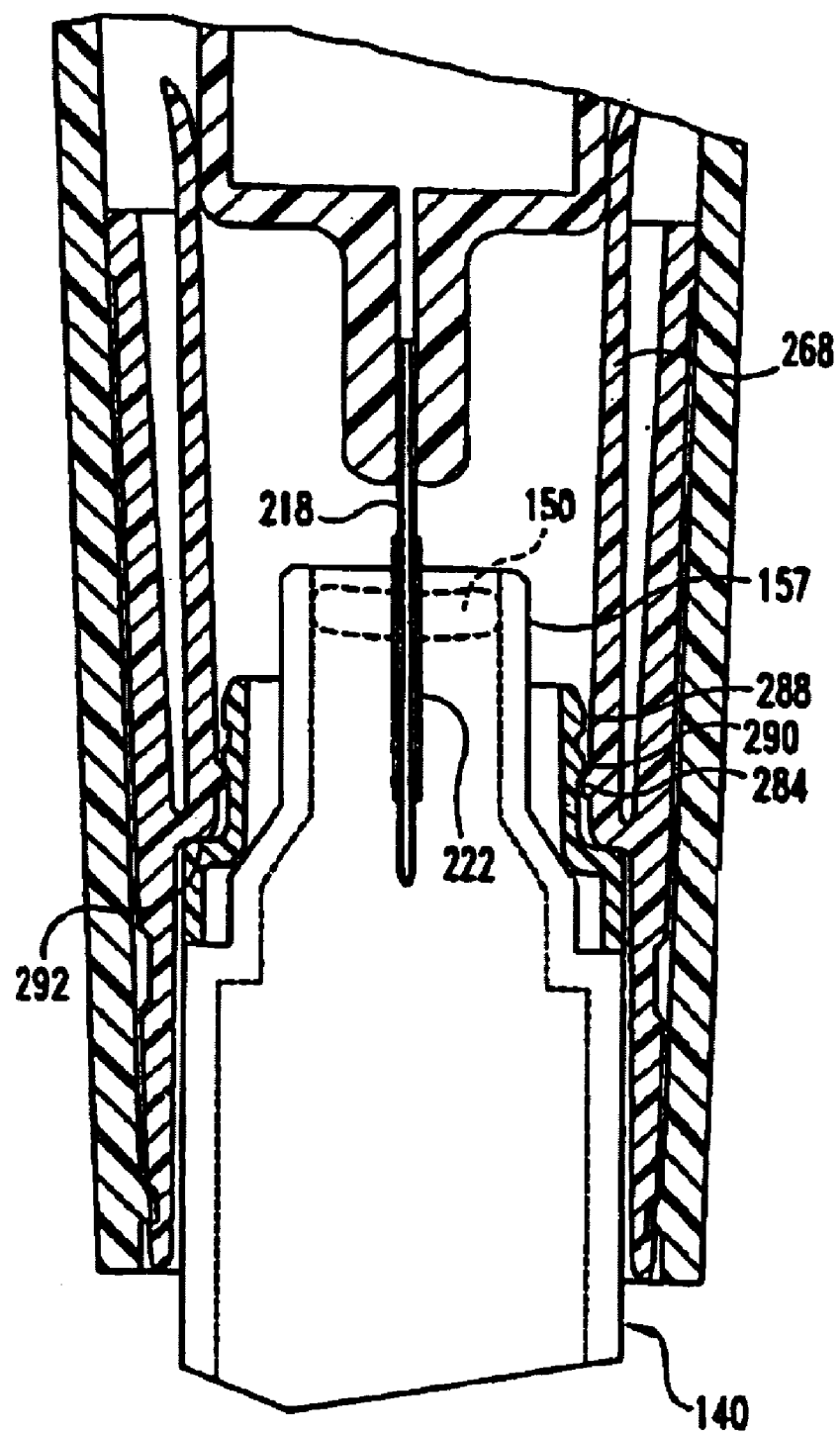
FIG. 10 is a cross-sectional, partial view similar to the view of FIG. 9, after insertion of an injection pen cartridge.

The structure of reconstituting appliance 200 will be further understood in view of the following explanation of its operation. When the lyophilized drug 30 of cartridge 140 is to be reconstituted, the needle shield assembly is first removed from its shipped position shown in FIGS. 8 and 9. Then, and with direction taken from the perspective of a viewer of FIG. 9, which does not show the needle shield assembly so removed, cartridge end 157 is inserted upward through the aligned opening in body end 234 and nose piece end 271 and within nose piece interior volume 269 until it enters collar interior volume 280 and abuts alignment collar 274. In the shown embodiment, alignment collar 274 is designed such that cartridge 140 abuts the annular end surface 277 of cylindrical base portion 276, but in alternate embodiments different regions of the collar, such as the interior surface of annular shoulder 292, could be abutted. After the initial abutment, as the user applies sufficient additional insertion force on cartridge 140, due to the resilient construction of nose piece 260 and alignment collar 274, ridge 284 slides over detents 302 and into the space between detents 302 and annular shoulder 292 as alignment collar 274 quickly moves proximally within both nose piece 260 and body 230, closing gap 294, until annular shoulder 292 abuts the underside of tubular portion 268, at which time the shifting of alignment collar 274 is halted. This sudden sliding movement of alignment collar 274, which started as the detents 302 move over ridge 284 and is halted by shoulder 292 abutting nose piece portion 268, provides a tactile signal, and preferably an audible signal, which can be perceived by an attentive user who then knows the cartridge is fully inserted, as visually such a determination is difficult as the needle 218 is hidden from side view within the housing assembly. At this full insertion point, which is shown in FIG. 10, both needle 218 and collar 222 span the cartridge stopper 150 to permit venting of the cartridge as diluent fluid contained within the syringe is laterally ejected through needle 218 into cartridge 140 by the depressing of appliance plunger 214. After the diluent fluid is introduced therein, cartridge 140 is withdrawn from the appliance, which withdrawal process does not pull out alignment collar 274. After cartridge withdrawal, end cap 315 is placed into the opening of body end 234 and frictionally fits with nose piece 260 to keep the needle and collar covered during disposal of appliance 200. Cartridge 140 can then be used with an injector pen in a conventional manner.

While this invention has been shown and described as having multiple designs, the present invention may be modified within the spirit and scope of this disclosure. For example, the reconstituting appliance need not include a shiftable alignment collar to function. This application is therefore intended to cover any variations, uses or adaptations of the invention using its general principles. Further, this application is intended to cover such departures from the present disclosure as come within known or customary practice in the art to which this invention pertains.

We claim:

1. A kit for reconstituting a quantity of a lyophilized drug in a cartridge to be used in an injection pen, comprising:
   a) an injection pen cartridge including:
      i) a barrel with at least one interior wall defining an internal reservoir partially filled with a quantity of a lyophilized drug and having an open proximal end and an open distal end;
      ii) a needle-penetrable stopper in sealed engagement with said proximal end of said barrel and having a stopper height;
      iii) a plunger slidably disposed within said distal end of said barrel and in sealed engagement with the interior wall of said barrel; and
   b) a reconstituting appliance including:
      i) a syringe body with at least one interior wall defining a fluid reservoir containing a diluent fluid and having an open proximal end and an open distal end;
      ii) a plunger slidably disposed within said proximal end of said syringe body and in sealed engagement with the interior wall of said syringe body;
      iii) an actuating member extending from said plunger beyond said proximal end of said syringe body and manually shiftable to effect movement of said plunger to force diluent fluid from said fluid reservoir through said open distal end of said syringe body;
      iv) a cannula defining an axial passage therethrough and having a proximal end and a closed distal end, said cannula proximal end in communication with the fluid reservoir through said open distal end of said syringe body, wherein said cannula has a length greater than said stopper height and wherein the distal end of said cannula terminates in a piercing tip;
      v) the distal end of said cannula defining a side port in communication with the axial passage, the side port being configured to direct fluid passing therethrough toward the interior wall of said barrel of said cartridge at an angle diverging from the axial direction of said cannula;
      vi) a housing having a needle covering portion extending around said cannula, said needle covering portion including a distal end having an opening in communication with an interior hollow of said needle covering portion which is structured and arranged to receive the proximal end of said barrel of said injection pen cartridge when inserted proximally within said opening, wherein said distal end of said needle covering portion is positioned distally of said cannula distal end;
      vii) a cartridge alignment member retained within said needle covering portion at a first axial position and defining an interior hollow structured and arranged to receive the proximal end of said barrel of said injection pen cartridge when said cartridge is proximally inserted through said opening of said needle covering portion distal end, said cartridge alignment member adapted to be abutted by said injection pen cartridge during proximal insertion of said cartridge and axially shifted relative to said needle covering portion to a second axial position at which said cannula extends through said stopper of said injection pen cartridge for drug reconstituting, wherein said cartridge alignment member comprises a tubular base portion with a stepped-down neck portion, wherein said neck portion fits within a tubular section of said needle covering portion in which fits the distal end of said syringe body, and wherein an intersection of said base portion and said neck portion defines an annular shoulder that directly abuts said tubular section when said cartridge alignment member is disposed in said second axial position; and viii) wherein said cannula distal end is hidden from side view by at least one of said needle covering portion and said cartridge alignment member as said cannula is introduced through said stopper of said injection pen cartridge.

2. The kit of claim 1 wherein said cartridge alignment member is retained within said needle covering portion at said first axial position by at least one projection from said tubular section of said needle covering portion that fits within a recess defined by axially spaced projecting portions of said stepped-down neck portion.

3. A method for reconstituting a quantity of a lyophilized drug in an injection pen cartridge, comprising the steps of:

a) providing an injection pen cartridge including a cartridge reservoir partially filled with a quantity of a lyophilized drug, wherein said cartridge is sealed with a needle penetrable stopper at one end and sealed with a plunger at the opposing end;

b) providing a reconstituting appliance which holds a quantity of diluent fluid and includes a needle and a housing, wherein said housing hides said needle from lateral view and defines an interior hollow around the needle which is shaped to accommodate said cartridge end with the stopper, and providing an alignment collar within said housing interior hollow which is axially shiftable from a first position to a second position by contact with said cartridge during insertion of said cartridge end with the stopper into said housing interior hollow to indicate a completed insertion to a user;

c) inserting said cartridge end with the stopper into said housing interior hollow such that said needle penetrates said stopper, wherein said needle terminates in a distal end within said cartridge reservoir;

d) laterally injecting said quantity of diluent fluid through a side port in the distal end of said needle into said cartridge reservoir above the level of said lyophilized drug; and e) after fluid injection, withdrawing said cartridge end with the stopper from said housing interior hollow, whereby said needle is removed from said stopper.

4. The method of claim 3 further comprising providing a venting collar mounted around said needle and which, during said cartridge end insertion step, penetrates said stopper so as to extend therethrough, and further comprising the step of releasing gas pressure from said cartridge reservoir during said fluid injection through a passage between said venting collar and said needle, wherein said passage extends from said cartridge reservoir past said stopper.

5. The method of claim 4 wherein said needle and said venting collar penetrate said stopper at an angle substantially perpendicular to said stopper.

6. The method of claim 3 and further comprising the steps of:

a) loading said cartridge into an injector pen;
b) selecting a dosage; and
c) injecting the selected dosage of the reconstituted drug into a person who needs a dosage of the drug.

7. A kit for reconstituting a quantity of a lyophilized drug in a cartridge to be used in an injection pen, comprising:

a) an injection pen cartridge including:
 i) a barrel with at least one interior wall defining an internal reservoir partially filled with a quantity of a lyophilized drug and having an open proximal end and an open distal end;
 ii) a needle-penetrable stopper in sealed engagement with said proximal end of said barrel and having a stopper height;
 iii) a plunger slidably disposed within said distal end of said barrel and in sealed engagement with the interior wall of said barrel; and b) a reconstituting appliance including:
 i) a syringe body with at least one interior wall defining a fluid reservoir containing a diluent fluid and having an open proximal end and an open distal end;
 ii) a plunger slidably disposed within said proximal end of said syringe body and in sealed engagement with the interior wall of said syringe body;
 iii) an actuating member extending from said plunger beyond said proximal end of said syringe body and manually shiftable to effect movement of said plunger to force diluent fluid from said fluid reservoir through said open distal end of said syringe body;
 iv) a cannula defining an axial passage therethrough and having a proximal end and a closed distal end, said cannula proximal end in communication with the fluid reservoir through said open distal end of said syringe body, wherein said cannula has a length greater than said stopper height and wherein the distal end of said cannula terminates in a piercing tip;
 v) the distal end of said cannula defining a side port in communication with the axial passage, the side port being configured to direct fluid passing therethrough toward the interior wall of said barrel of said cartridge at an angle diverging from the axial direction of said cannula;
 vi) a housing having a needle covering portion extending around said cannula, said needle covering portion including a distal end having an opening in communication with an interior hollow of said needle covering portion which is structured and arranged to receive the proximal end of said barrel of said injection pen cartridge when inserted proximally within said opening, wherein said distal end of said needle covering portion is positioned distally of said cannula distal end;
 vii) a cartridge alignment member retained within said needle covering portion at a first axial position and defining an interior hollow structured and arranged to receive the proximal end of said barrel of said injection pen cartridge when said cartridge is proximally inserted through said opening of said needle covering portion distal end, said cartridge alignment member adapted to be abutted by said injection pen cartridge during proximal insertion of said cartridge and axially shifted relative to said needle covering portion to a second axial position at which said cannula extends through said stopper of said injection pen cartridge for drug reconstituting, wherein said cartridge alignment member includes a shoulder that directly abuts a stop member of said needle covering portion when said cartridge alignment member is disposed in said second axial position; and viii) wherein said cannula distal end is hidden from side view by at least one of said needle covering portion and said cartridge alignment member as said cannula is introduced through said stopper of said injection pen cartridge.

8. A kit for reconstituting a quantity of a lyophilized drug in a cartridge to be used in an injection pen, comprising:
   a) an injection pen cartridge including:
      i) a barrel with at least one interior wall defining an internal reservoir partially filled with a quantity of a lyophilized drug and having an open proximal end and an open distal end;
      ii) a needle-penetrable stopper in sealed engagement with said proximal end of said barrel and having a stopper height;
      iii) a plunger slidably disposed within said distal end of said barrel and in sealed engagement with the interior wall of said barrel; and
   b) a reconstituting appliance including:
      i) a syringe body with at least one interior wall defining a fluid reservoir containing a diluent fluid and having an open proximal end and an open distal end;
      ii) a plunger slidably disposed within said proximal end of said syringe body and in sealed engagement with the interior wall of said syringe body;
      iii) an actuating member extending from said plunger beyond said proximal end of said syringe body and manually shiftable to effect movement of said plunger to force diluent fluid from said fluid reservoir through said open distal end of said syringe body;
      iv) a cannula defining an axial passage therethrough and having a proximal end and a closed distal end, said cannula proximal end in communication with the fluid reservoir through said open distal end of said syringe body, wherein said cannula has a length greater than said stopper height and wherein the distal end of said cannula terminates in a piercing tip;
      v) the distal end of said cannula defining a side port in communication with the axial passage, the side port being configured to direct fluid passing therethrough toward the interior wall of said barrel of said cartridge at an angle diverging from the axial direction of said cannula;
      vi) a housing having a needle covering portion extending around said cannula, said needle covering portion including a distal end having an opening in communication with an interior hollow of said needle covering portion which is structured and arranged to receive the proximal end of said barrel of said injection pen cartridge when inserted proximally within said opening, wherein said distal end of said needle covering portion is positioned distally of said cannula distal end;
      vii) a cartridge alignment member retained within said needle covering portion at a first axial position and defining an interior hollow structured and arranged to receive the proximal end of said barrel of said injection pen cartridge when said cartridge is proximally inserted through said opening of said needle covering portion distal end, said cartridge alignment member adapted to be abutted by said injection pen cartridge during proximal insertion of said cartridge and axially shifted relative to said needle covering portion to a second axial position at which said cannula extends through said stopper of said injection pen cartridge for drug reconstituting, wherein said cartridge alignment member is retained within said needle covering portion at said first axial position by at least one projection of said needle covering portion that fits within a recess defined by axially spaced projecting portions of said alignment member; and
      viii) wherein said cannula distal end is hidden from side view by at least one of said needle covering portion and said cartridge alignment member as said cannula is introduced through said stopper of said injection pen cartridge.

9. A kit for reconstituting a quantity of a lyophilized drug in a cartridge to be used in an injection pen, comprising:
   a) an injection pen cartridge including:
      i) a barrel with at least one interior wall defining an internal reservoir partially filled with a quantity of a lyophilized drug and having an open proximal end and an open distal end;
      ii) a needle-penetrable stopper in sealed engagement with said proximal end of said barrel and having a stopper height;
      iii) a plunger slidably disposed within said distal end of said barrel and in sealed engagement with the interior wall of said barrel; and
   b) a reconstituting appliance including:
      i) a syringe body with at least one interior wall defining a fluid reservoir containing a diluent fluid and having an open proximal end and an open distal end;
      ii) a plunger slidably disposed within said proximal end of said syringe body and in sealed engagement with the interior wall of said syringe body;
      iii) an actuating member extending from said plunger beyond said proximal end of said syringe body and manually shiftable to effect movement of said plunger to force diluent fluid from said fluid reservoir through said open distal end of said syringe body;
      iv) a cannula defining an axial passage therethrough and having a proximal end and a closed distal end, said cannula proximal end in communication with the fluid reservoir through said open distal end of said syringe body, wherein said cannula has a length greater than said stopper height and wherein the distal end of said cannula terminates in a piercing tip;
      v) the distal end of said cannula defining a side port in communication with the axial passage, the side port being configured to direct fluid passing therethrough toward the interior wall of said barrel of said cartridge at an angle diverging from the axial direction of said cannula;
      vi) a housing having a needle covering portion extending around said cannula, said needle covering portion including a distal end having an opening in communication with an interior hollow of said needle covering portion which is structured and arranged to receive the proximal end of said barrel of said injection pen cartridge when inserted proximally within said opening, wherein said distal end of said needle covering portion is positioned distally of said cannula distal end;

vii) a cartridge alignment member retained within said needle covering portion at a first axial position and defining an interior hollow structured and arranged to receive the proximal end of said barrel of said injection pen cartridge when said cartridge is proximally inserted through said opening of said needle covering portion distal end, said cartridge alignment member adapted to be abutted by said injection pen cartridge during proximal insertion of said cartridge and axially shifted relative to said needle covering portion to a second axial position at which said cannula extends through said stopper of said injection pen cartridge for drug reconstituting;

viii) wherein said cannula distal end is hidden from side view by at least one of said needle covering portion and said cartridge alignment member as said cannula is introduced through said stopper of said injection pen cartridge; and ix) a collar fixedly mounted around a portion of said cannula and defining an axial venting passage between said cannula and said collar, wherein said collar extends through said stopper for venting said injection pen cartridge when said alignment member has been axially shifted within said needle covering portion to said second axial position by abutting contact with said injection pen cartridge during proximal insertion of said cartridge.

* * * * *